(12) United States Patent
Forte et al.

(10) Patent No.: US 7,819,821 B2
(45) Date of Patent: Oct. 26, 2010

(54) URINE COLLECTION DEVICE

(75) Inventors: Vincent John Charles Forte, Suffolk (GB); David Edward Maddison, West Sussex (GB)

(73) Assignee: Funnelly Enough Limited, London, Great Britain (GB)

( * ) Notice: Subject to any disclaimer, the term of this patent is extended or adjusted under 35 U.S.C. 154(b) by 0 days.

(21) Appl. No.: 11/861,458

(22) Filed: Sep. 26, 2007
(Under 37 CFR 1.47)

(65) Prior Publication Data
US 2008/0228106 A1 Sep. 18, 2008

(30) Foreign Application Priority Data

| Sep. 30, 2006 | (GB) | ................................. 0619356.9 |
| Feb. 16, 2007 | (GB) | ................................. 0703003.4 |
| Aug. 30, 2007 | (GB) | ................................. 0716848.7 |

(51) Int. Cl.
A61B 5/20 (2006.01)
(52) U.S. Cl. ........................................ 600/573; 600/574
(58) Field of Classification Search ................ 600/573, 600/574, 576, 579
See application file for complete search history.

(56) References Cited

U.S. PATENT DOCUMENTS

| 3,830,107 A |   | 8/1974 | Linzer |
| 3,943,770 A |   | 3/1976 | McDonald |
| 4,276,889 A |   | 7/1981 | Kuntz et al. |
| 4,301,812 A |   | 11/1981 | Layton et al. |
| 4,492,258 A |   | 1/1985 | Lichtenstein et al. |
| 4,494,581 A | * | 1/1985 | Gordon ........................... 141/1 |
| 4,495,951 A |   | 1/1985 | Kenda |
| 5,566,708 A | * | 10/1996 | Hobbs, Jr. .................... 137/360 |
| 5,611,768 A | * | 3/1997 | Tutrone, Jr. ................... 600/29 |
| 5,918,913 A | * | 7/1999 | Lewis et al. ............. 285/148.14 |
| 6,730,057 B2 | * | 5/2004 | Zhao et al. ..................... 604/11 |
| 2002/0193760 A1 | * | 12/2002 | Thompson .................. 604/318 |
| 2004/0267158 A1 | * | 12/2004 | Paasch et al. ............... 600/573 |
| 2005/0004538 A1 | * | 1/2005 | Forte ........................... 604/327 |
| 2006/0064033 A1 | * | 3/2006 | Stewart et al. .............. 600/573 |
| 2006/0149164 A1 | * | 7/2006 | Lee et al. ..................... 600/573 |

FOREIGN PATENT DOCUMENTS

| CA | 2170936 | 9/1996 |
| DE | 3826376 | 3/1989 |

(Continued)

*Primary Examiner*—Max Hindenburg
*Assistant Examiner*—Michael C Stout
(74) *Attorney, Agent, or Firm*—Hahn Loeser + Parks LLP; Scott M. Oldham, Esq.

(57) ABSTRACT

A urine collection device comprises a collector to collect urine voided by a user; first and second outlets adapted to allow urine collected by the collector to drain from the device and a transfer passage adapted to transfer urine collected by the collector to a receptacle. The first outlet includes a flow rate variation device so constructed and arranged that an initial drain flow rate through the variation device is greater than a second drain flow rate through the variation device; and the second outlet comprises an overflow outlet adapted to allow urine collected by the collector to drain from the urine collection device at a third drain flow rate equal to or higher than the initial drain flow rate through the variation device.

33 Claims, 3 Drawing Sheets

FOREIGN PATENT DOCUMENTS

| | | |
|---|---|---|
| EP | 0009980 | 4/1980 |
| EP | 0218758 | 4/1987 |
| EP | 0373917 | 6/1990 |
| EP | 1401334 | 3/2004 |
| GB | 1 574 864 A | 9/1980 |
| GB | 2247626 | 3/1992 |
| GB | 2362577 | 11/2001 |
| GB | 2385532 | 8/2003 |
| WO | 8505550 | 12/1985 |
| WO | 84/03213 A | 10/1990 |
| WO | 02/094104 A | 11/2002 |
| WO | 2005003725 | 1/2005 |

* cited by examiner

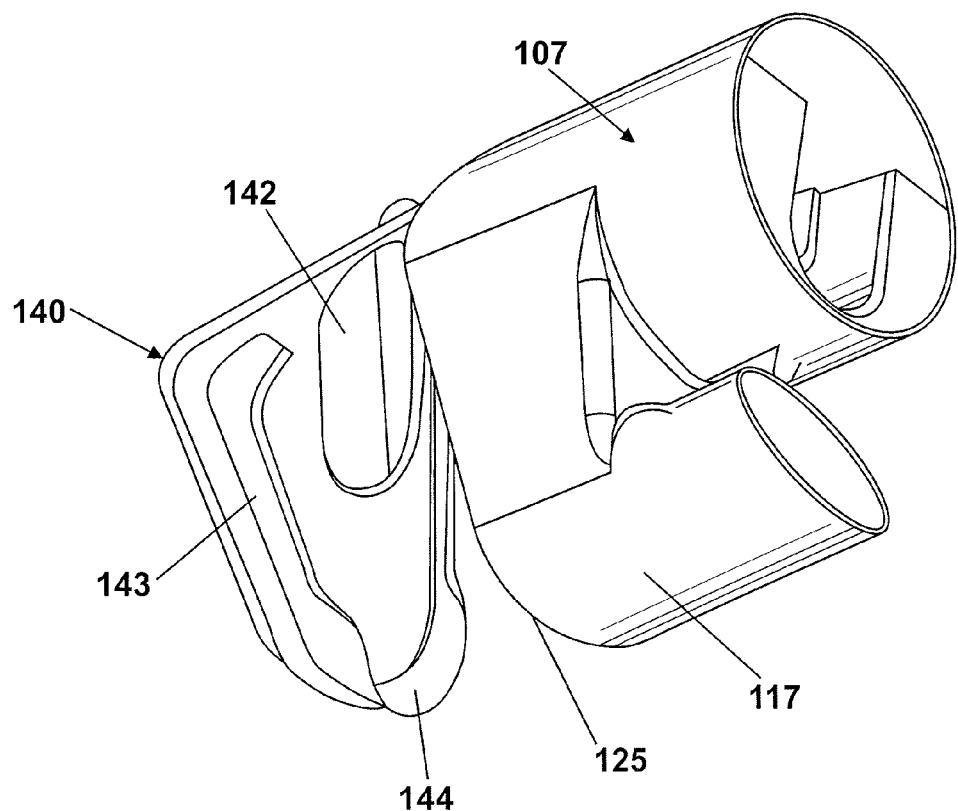
*Fig. 5*
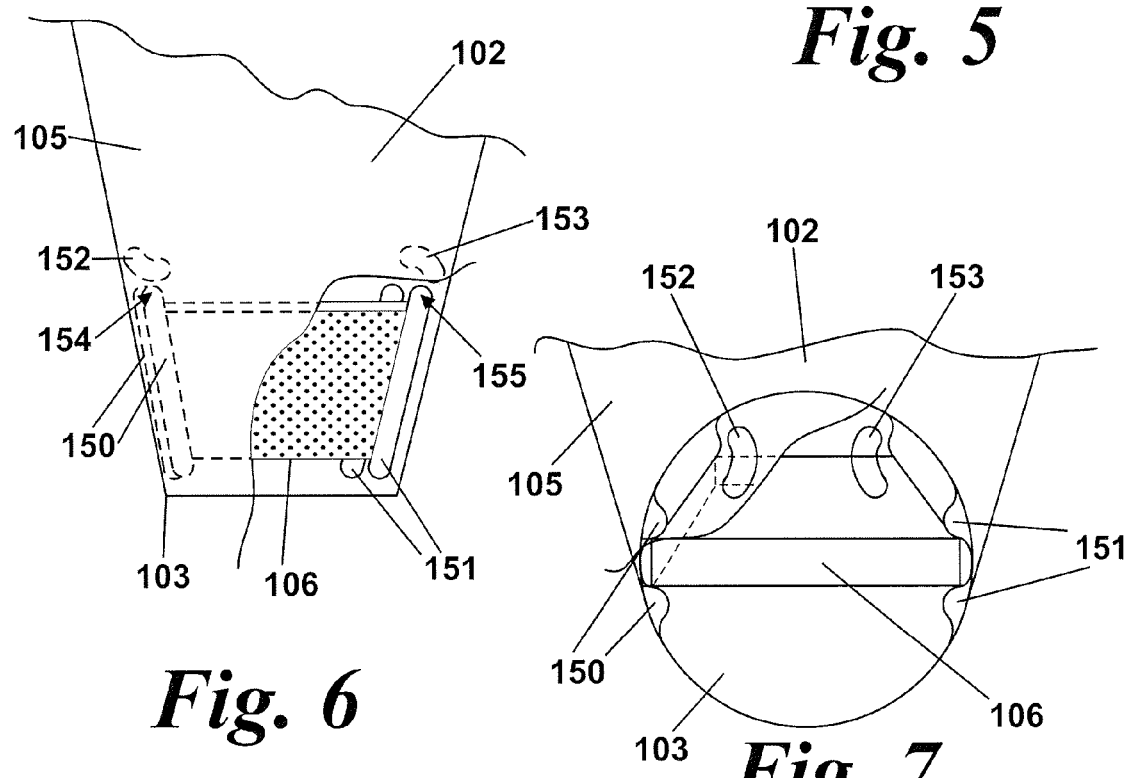
*Fig. 6*
*Fig. 7*

URINE COLLECTION DEVICE

This invention relates to a device to assist in the collection of urine from a patient.

TECHNICAL FIELD

The analysis of a patient's urine is often used as a diagnostic method for detecting a wide range of conditions and illnesses. The urine can be analysed for particular chemicals that are indicative of particular infections, for example. Analysis of a mid stream urine sample is preferred for accurate results, as it is thought to be more representative of the state of the urine. As its name implies, a mid stream sample should not contain urine from the initial flow.

The patient is typically required to provide a urine sample into a sample bottle. In general, sample bottles are relatively small and have a narrow neck, making it difficult for the patient to accurately deliver a sample into the bottle. Due to these difficulties, providing a urine sample can be a messy and unpleasant process especially if a mid stream sample is required. The difficulties are particularly acute when the patient is female, due to the problem of locating the sample bottle correctly.

BACKGROUND OF THE INVENTION

Prior art devices have been made to assist patients in delivering a sample. EP 1 401 334 discloses a device having a collection funnel that automatically expands from its flat-packed storage configuration into a usable configuration, thereby making locating the device appropriately easier. The device has an outlet to which a sample bottle can be placed for easier collection. However, this device does not address the issue of ensuring the effective filling of a sample bottle, while ensuring the collection funnel does not overflow. It does not make provision for taking a mid stream sample, either.

Further, GB 2 385 532 discloses a urine sample collection device that is adapted to collect a mid stream urine sample. The device has means to divert the initial flow of urine away from an aperture to which a sample bottle is connected. As the urine flow increases, urine enters the aperture. As this device depends on the urine flow rate it may be unreliable at collecting a mid stream sample.

BRIEF SUMMARY OF THE INVENTION

According to an example of the invention, a urine collection device comprises a collection system to collect urine voided by a user, having a first and second outlet adapted to allow urine collected to drain from the device. A transfer passage is adapted to transfer urine to a receptacle. The first outlet may include a flow rate variation device so constructed and arranged that an initial drain flow rate through the variation device is greater than a second drain flow rate through the variation device. The second outlet comprises an overflow outlet adapted to allow collected urine to drain from the urine collection device at a third drain flow rate equal to or higher than the initial drain flow rate through the variation device.

The provision of the two outlets and the flow rate variation device ensures that the midstream sample can be collected easily, since the initial flow drains relatively quickly through the first outlet, the subsequent flow drains more slowly through the first outlet to allow the midstream to be transferred to the receptacle, and then the overflow outlet is operative, if necessary, once the receptacle is full. This allows the further flow to drain more quickly to prevent the collection system from overflowing.

The flow rate variation device may comprise an expandable plug accommodated in the base of the collection system. The plug initially allows a greater initial drain flow rate, but expands on contact with liquid to provide the second reduced drain flow rate.

The plug is conveniently formed of a sponge material. The sponge material may be biodegradable.

The transfer passage may be formed in a transfer device connected to the collection system. The transfer device is also adapted for connection to the receptacle, such as a sample bottle. The transfer device may have a connection, such as a connecting collar adapted to receive and retain a sample bottle by an interference fit. Alternatively, the connection system may comprise a screw thread for the sample bottle.

The transfer device may comprise the transfer passage and the overflow outlet. The transfer passage allows urine to flow from the collection system into the receptacle when the urine in the collection system reaches a first predetermined level, and the overflow outlet allows urine flow to drain once the level in the receptacle reaches a second predetermined level.

The overflow outlet may comprise a passage arranged to at least one side of the transfer passage to divert flow away from the receptacle.

The transfer passage may be generally U-shaped, having a base which forms a weir over which urine flows from the collection system into the receptacle. The top of the transfer passage forms a further weir over which urine flows to the overflow passage.

The overflow passage directs the overflow urine on at least one side of the transfer passage and through an outlet below the receptacle. The outlet may be suitably shaped or shielded to direct the overflow away from the receptacle, to avoid the outside of the receptacle coming into contact with urine.

In an example, the urine collection device is so constructed and arranged that, in use, the sample bottle is inclined from an upright position. Thus, when the device has been used and the bottle is turned to be upright, the bottle is not full to its brim. The risk of spillage when the sample bottle is removed from the connection system is reduced. A cap can then be placed on the bottle without tainting the user's hands. The device may further be arranged that a portion of the device extends into the bottle thereby displacing a proportion of its contents. This is advantageous as when the bottle is removed from the device, its effective capacity increases, which ensures that urine is not full to the brim of the bottle. The device is therefore hygienic.

The collection system may comprise a funnel-shaped member having a larger end and a narrower end. The larger end forms a receiving end for positioning adjacent the user in use. The first outlet is at the narrower end. The flow rate variation device may be inserted directly and may be glued into the narrower end of the funnel, or may be located by a separate member attached to the narrower end of the funnel.

The device is a single-use device, and for ease of use will normally be disposed of in a toilet. It must therefore be readily flushable and biodegradable. The material or materials used must be able to withstand urine at body temperature for a short time, so that the device keeps its shape in use, but then readily softens in water, to enable it to be flushed away. The device could be made of paper, in particular waxed paper, or a biodegradable polymer such as Plantic (RTM). It is also imperative that the material has no physico-chemical effect on the urine, either by contaminating it or absorption from it. The material may therefore be coated with a suitable inert substance.

The device, except for an expandable plug, may be injection moulded in one operation, which may be a multi-stage operation. Alternatively the funnel may be formed from a sheet template which is ultrasonically welded, glued or clipped together to form the funnel. The transfer device may be injection moulded onto the funnel, or be formed as a separate part which is glued or welded to the funnel. Where the flow rate variation device is an expandable plug, this is inserted into the funnel as a last stage in assembly. If the plug is located in a separate member, that member may be injection moulded and attached to the funnel in any suitable way.

In an example, the device is constructed and arranged such that it can be stored flat. It may include an automatic opening system to open the collection system from the flat storage configuration to an open configuration for use.

The flow rate variation device may be mounted in the collection system by rails. In particular, the rails may comprise a first pair of rails adapted to secure one side of the device and a second pair of rails adapted to secure the other side of the device. Further, end rails may be provided to prevent the flow rate variation device from sliding from between the first and second pairs of rails. Preferably the rails are injection moulded as part of the collection system. Alternatively, the flow rate variation device may be secured in the collection system by adhesive.

The collection system may include a coupling member to connect the transfer device to the collection system. Preferably, the coupling member includes a mounting projection that engages with the transfer device. The mounting projection may include a sealing skirt portion that is adapted to form a seal with the transfer device. The coupling member therefore provides a simple yet secure means of attaching the transfer device to the collection system, while being easy and cost effective to manufacture with the remainder of the device.

These and other advantages and novel features of the present invention, as well as details of an illustrated embodiment thereof, will be more fully understood from the following description and drawings.

BRIEF DESCRIPTION OF THE DRAWINGS

FIG. 5 shows a further embodiment of an attachment system for connecting the transfer device to the collection system;

FIG. 6 shows a detailed sectional side view of the outlet showing the expandable plug mounted therein; and FIG. 7 shows an end view of the outlet shown in FIG. 6.

DETAILED DESCRIPTION OF THE INVENTION

Figure 1:
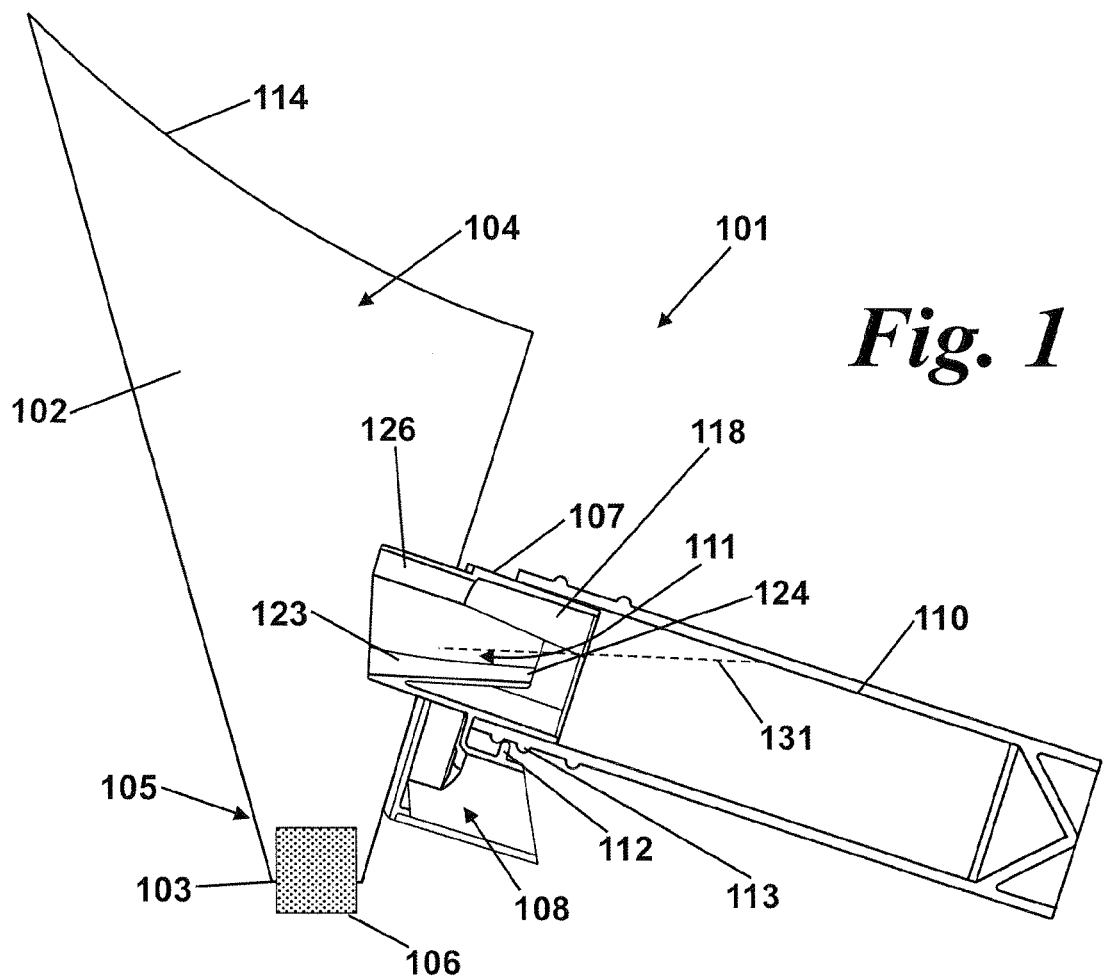
FIG. 1 shows a side view of an embodiment of the device of the invention.

The urine collection device 101, as shown in the drawings, is used to provide medical practitioners with urine samples for urinalysis.

FIG. 1 shows an embodiment of the urine collection device 101 of the invention. The device 101 comprises a collection system in the form of a funnel 102 having a larger end 104 and a narrower end 105. The larger end 104 forms a receiving end for placing adjacent a user to collect urine. A first outlet 103 is formed in the narrower end 105, which, when the device 101 is in use, is arranged to be the lowermost point. The first outlet 103 includes a flow rate variation device 106 mounted therein. The collection system 102 has a transfer device 107 affixed thereto, within which is formed a second outlet 108. The transfer device 107 is adapted to receive a receptacle 110 and includes a transfer passage 111 to enable urine collected by the collection system 102 to be transferred into the receptacle 110.

The collection system 102 comprises a funnel shaped member of flexible polymeric or paper material. However, although the funnel is flexible, it has sufficient rigidity to substantially maintain its shape when it is in use and contains urine. It may be of a polymeric material chosen to have the necessary degree of rigidity or alternatively it may have support ribs or reinforcing elements at predetermined locations. The polymeric material may be of a type that prevents liquid droplets forming on its surface to encourage urine collected in the funnel 102 to drain towards the outlet aperture 103. Alternatively, the collection system 102 may be coated in or treated with such a material. The collection system 102 includes an ergonomically shaped rim 114. The rim 114 is placed against the user's body when the device 101 is in use. The rim 114 is ergonomically shaped to fit comfortably against or adjacent to the patient's body while ensuring minimal spillage. Further, the rim 114 is formed at an angle such that when the device is in use and position adjacent the patient's body, the sample bottle 110 is at an angle to its upright position. This ensures that when the device 101 is in use, the sample bottle 110 will not fill to the brim thereby making it easier to handle when removing it from the transfer device 107.

The first outlet 103 comprises an aperture formed in the narrower end 105 of the funnel 102. The flow rate variation device 106 comprises an expandable plug of sponge material that is affixed in the outlet aperture 103 by adhesive. FIGS. 6 and 7 show an alternative means for mounting the expandable plug 106 in the outlet aperture 103 that is discussed in further detail below. The expandable plug 106 is shaped such that it does not block the outlet aperture 103 when it is dry. Thus, the expandable plug 106 will initially allow urine collected by the collection funnel 102 to flow both around it and out of the outlet aperture 103 and to soak through it and out of the outlet aperture 103. The expandable sponge 106 is adapted to expand when it gets wet and therefore, once sufficient urine has soaked in to it, it will expand to restrict the flow around it thereby only allowing urine to leave the funnel 102 by soaking through the sponge material. Thus, the expandable sponge plug 106 provides a first flow rate out of the device when it is dry and a second, reduced, flow rate out of the device when it is wet. The second flow rate is thereby determined, in part, by the porosity of the plug. It will be appreciated that the plug 106 need not block the outlet 103 when it gets wet, but simply needs to expand such that the size of the outlet 103 not blocked by the plug 106 is reduced to obtain the reduced second flow rate out of the device 101. It will also be appreciated that when the plug 106 is adapted to block the outlet 103, the second flow rate that urine will drain from the device can be altered by adjusting the porosity of the material from which the plug is made.

The position of the first outlet 103 means that when the device 101 is in use, the first outlet 103 is at the lowest point, enabling substantially all of the urine collected by the collection system 102 to drain away. Therefore the patient is not required to empty the device in any way when they have finished using the device, as the collection system 102 will empty in normal operation by virtue of the position of the first outlet 103. This feature further improves the hygiene for the patient when using the device 101.

The receptacle 110 comprises a sample bottle that is received on the transfer device 107 and held thereon by a securing flange 112 that engages with a standard external screw thread 113 on the receptacle 110.

Figure 2:
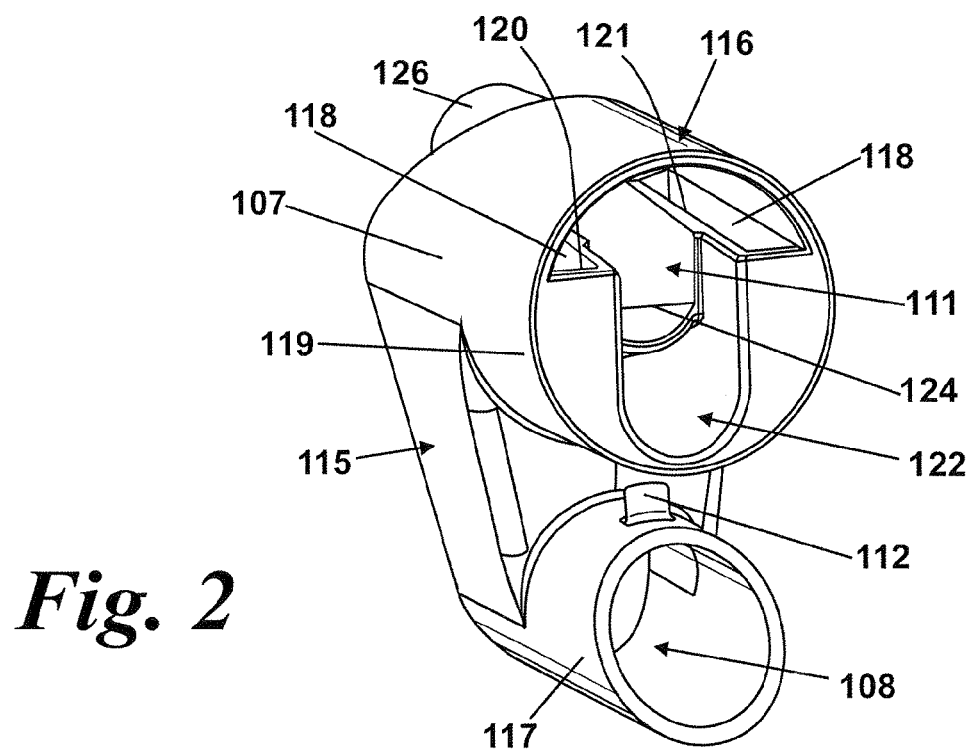
FIG. 2 shows a front view of the transfer device shown in FIG. 1.
Figure 3:
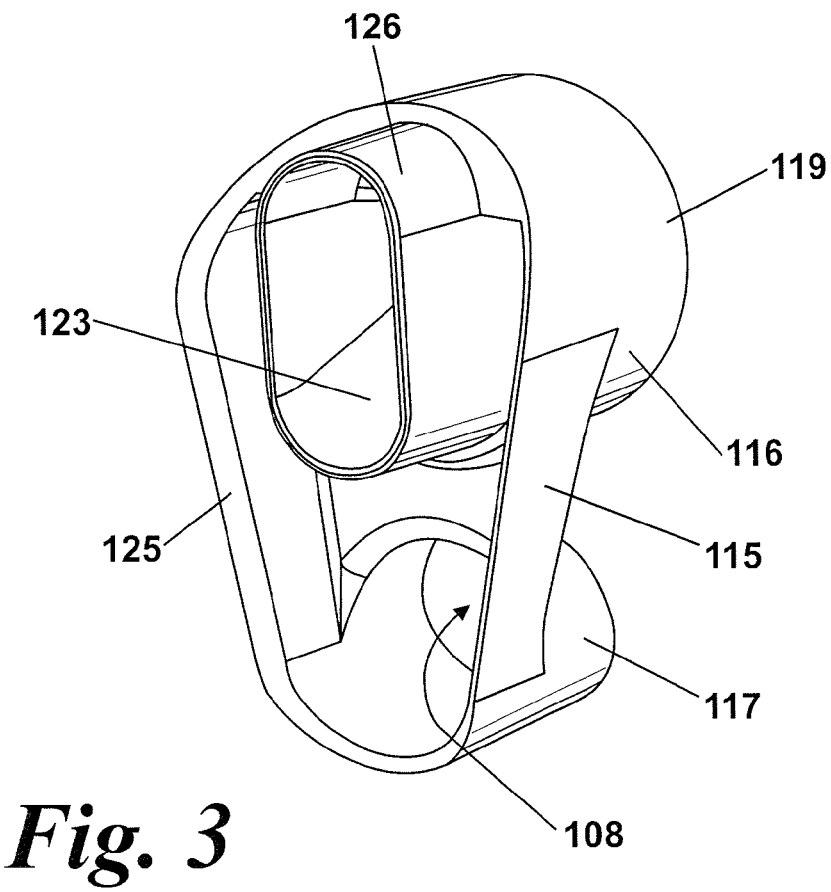
FIG. 3 shows a rear view of the transfer device detached from the collection system.

The transfer device 107 is shown in detail in FIGS. 2 and 3. The collection system 102 and the receptacle 110 have been omitted from these figures for clarity. The transfer device 107 comprises a body 115 having an upper tubular projection 116 adapted to be received within the mouth of the receptacle 110 and a lower tubular projection 117 that forms part of the second outlet means 108. The upper tubular portion 116 defines the transfer passage 111 and includes a connecting collar 119 that is sized to form an interference fit within the mouth of the receptacle 110. The lower tubular projection 117 ensures that urine flowing out of the second outlet 108 flows clear of the device 101 and therefore reduces the chance of urine coming into contact with the outside surfaces of the device 101 or the user's hands. The securing flange 112 extends from the lower tubular projection 117 toward the upper tubular projection 116.

The second outlet 108 includes an overflow outlet 118 comprising a weir formed in the upper tubular portion 116 of the transfer device 107. A passage means comprising two overflow channels 120, 121 located on opposed sides of the transfer passage 111 direct urine that passes over the weir 118 to leave the device through the second outlet 108. The channels 120, 121 are formed between the body 115 and the transfer passage 111.

The overflow outlet 118 is able to effectively drain urine from the device when the input rate is at least 50 ml/s. As the normal urine flow rate of a person is between 10 and 40 ml/s, the device allows the drainage of the initial flow of urine (approximately the first 10-20 ml) to obtain a mid-stream sample and the overflow outlet 118 will be able to drain urine at a sufficient rate to ensure the device does not overflow.

The transfer passage 111 comprises a U-shaped transfer channel 122, formed between the overflow channels 120, 121. The transfer passage 111 includes a base 123 that forms a weir 124 over which urine flows to enter the sample bottle 110. Thus, the overflow outlet weir 118 is located at the top of the transfer passage 111 such that when the urine flow is high or when the sample bottle 110 is full and the level rises, urine is able to flow out of the device 101 via the overflow weir 118, channels 120, 121 and the second outlet 108.

FIG. 3 shows the back of the transfer device 107 without the collection system 102 attached. The transfer device 107 includes a peripheral rim 125 to which the collection system 102 is affixed. In the present embodiment the collection system 102 and the transfer device 107 are formed integrally as a single moulding, but alternatively, the collection system 102 may be affixed by adhesive to rim 125. The collection system 102 closes the body 115 of the transfer device 107 such that only a transfer port 126 of the upper projection 116 extends into the collection system 102.

The device 101 may also have automatic opening system or means (not shown). The collection system 102 is flexible such that the device 101 can be stored in a substantially flat configuration. Once removed from any packaging, for example, the automatic opening means bias the collection system 102 into an open configuration. In the open configuration the collection system 2 adopts its funnel-like appearance and is thus prepared for receiving urine. The device may be self-opening, if the material is such that it provides the necessary resilience. Alternatively, a separate resilient means or member may be used to open the device and the device may have hinged portions as necessary.

The material chosen for the device 101 should be biodegradable and flushable, in other words it can be flushed away in a toilet, for example, after use. Any polymeric material must therefore be of a grade that softens in water, but is sufficiently strong that the integrity of the device is not compromised for the duration that urine could be expected to flow through the device. Thus, a material that can resist waA urine for 1 to 2 minutes before losing its integrity is preferable. Alternatively, the internal surface of the device may have a wax coating to prevent premature softening of the material of the device. Alternatively, the material may be a composite of high and low temperature resistant grades of polymeric material. Polymers made from plant materials, are suitable, as is paper, in particular waxed paper. If needed, the device 101 may have a protective coating (not shown) at least on its surfaces that would be in contact with any urine in normal use. The protective coating ensures that the urine sample being collected does not absorb any chemicals from the material of the device or vice versa, as that could affect the results of any subsequent medical analysis.

The device 101 is a single moulding, except for the expandable sponge 106, and is formed of biodegradable Plantic (RTM) material.

In use, a patient removes the device 101 from its packaging and allows it to automatically open from its flat storage configuration into the open configuration by way of automatic opening means that bias the device to the open position. The sample bottle 110 is attached to the device by pushing it onto the collar 119 to form an interference fit and thus engaging the securing flange 112 with the screw thread 113. The sample bottle 110 is preferably attached by a quarter-turn or at least a half-turn, but the degree of turn can be adjusted by changing the position of the securing flange 112 on the lower tubular projection 117. The device 101 is constructed and arranged such that in use the sample bottle 110 is inclined to its upright position as shown in FIG. 1. The user places the device 101 in the appropriate position with the rim 114 adjacent their body. Urine can then be voided into the funnel shaped collection system 102. The user may hold the device 101 by the gripping portion 114. The gripping portion 114 is positioned such that, in use, it is above the level of the urine collected within the funnel and above the level at which it exits the user, preventing it from reaching the user's fingers holding the gripping portion 114. Therefore, the device is hygienic.

The initial flow received by the funnel 102 will drain to the narrower end 105 and leave the device 101 via the first outlet 103. In doing so the expandable sponge 106 will expand as described above thereby reducing the flow rate out of the device via the first outlet 103. Thus, the initial flow of urine, which is considered unsuitable for accurate urinalysis, is discarded from the funnel 102. The reduction in flow rate caused by the expansion of the expandable sponge 106 is such that under a range of typical urine flow rates, the level of urine in the funnel 102 will begin to rise.

When the urine level reaches the transfer port 126, it will begin to flow into the transfer passage 111 along base 123 and over weir 124 into the sample bottle 110. The urine level in the funnel 102 will continue to rise once the sample bottle 110 is filled to the predetermined level designated by dashed line 131. At this point, the urine will flow over the overflow weirs 118 and into overflow channels 120, 121 which guide the urine out of the device 101 through the second outlet 108.

Once the user has finished voiding urine, if the level is above line 131, urine will drain over the overflow weir 118 in combination with the first outlet 103. When the level has fallen below level 131, urine will drain from the funnel 102 through the first outlet 103 by soaking through the expandable sponge 106 until the funnel 102 is empty.

The sample bottle 110 can then be removed from the device 102 by overcoming the interference fit between the bottle 110 and the collar 119 and unscrewing it from engagement with the securing flange 112. As the bottle 110 is inclined to its upright position in use, when it is returned to an upright position the urine is not full to the brim and thus removal of the bottle is clean and easy. The risk of spillage is further reduced as a portion of the transfer device 107 extends into the neck of the bottle 110, thereby displacing a corresponding proportion of the bottle's contents. Thus, when the bottle 110 is removed, the urine is not full to the brim. A cap (not shown) can then be screwed on to the bottle 110 to seal it.

Figure 4:
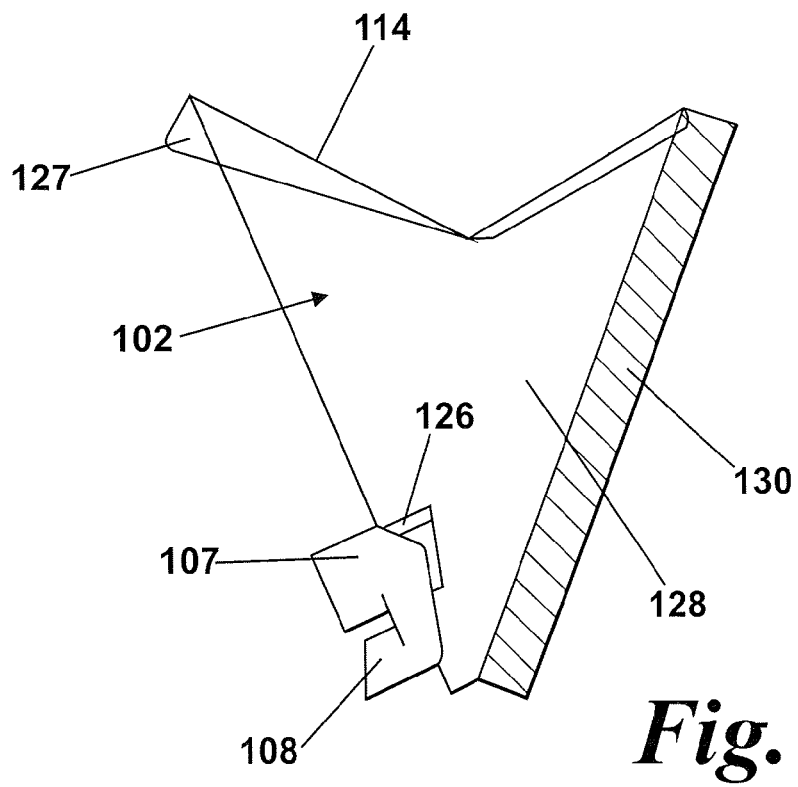
FIG. 4 shows a further embodiment of the collection system.

FIG. 4 shows another embodiment of the collection system 102 where the rim 114 includes a gripping portion 127. Corresponding reference numerals have been applied to corresponding parts. The gripping portion comprises an outwardly turned flange that the user can use to hold the device 101 when in use. The funnel 102 comprises a flat sheet member 128 that is folded to form the funnel shape and is secured in that shape by a securing clip 130. It may alternatively be ultrasonically welded or glued. The flat sheet member 128 is of Plantic (RTM) material, with the transfer device 107 being formed as a separate member also of Plantic (RTM) and glued or welded to the funnel. The transfer device may instead be injection moulded onto the funnel. The sponge 106 is then inserted separately.

FIG. 5 shows a modification of the device of FIG. 1, of an attachment means 140 for connecting the transfer device 107 to the collection system 102. Corresponding reference numerals have been applied to corresponding parts. The attachment means comprises a coupling member that is adapted to be secured to the collection system 102 and includes means to attach the transfer device 107. The attachment means 140 comprises a generally triangular body 141 having rounded corners. The body 141 is curved to enable it to be secured to the collection system 102 without disrupting the profile of the collection system funnel 102 when it is in its in use configuration. The attachment means 140 is secured to the collection system 102 by adhesive, although it may be secured by direct injection moulding or ultrasonic welding or any other appropriate means. The body 141 also includes an aperture 142 and a mounting projection 143. The aperture 142 is adapted to align with a corresponding aperture (not shown) in the collection system 102 when the attachment means is secured to the collection system 102. The aperture 142 is also adapted to allow the transfer port 126 to extend therethrough into the collection system 102 similar to that shown in the embodiment of FIG. 1. The mounting projection 143 comprises a substantially U-shaped flange that extends from the body 141. A portion 144 of the flange extends at a greater height from the body 141 than the remainder of the flange forming a sealing skirt that is adapted to abut and sealingly engage with the lower tubular projection 117 of the transfer device 107. Thus, when assembled, the transfer port 126 sealingly engages with body 141 surrounding the aperture 142 and the transfer device 107 is sealingly received within the mounting projection 143 such that the rim 125 abuts the body 141. The outside surface of the transfer device 107 adjacent the rim 125 therefore forms an interference fit with the mounting projection 143 and skirt 144. It will be appreciated that adhesive could also be used to secure the transfer device 107 to the mounting projection 143.

In this embodiment the collection system 102, the transfer device 107 and the attachment means 140 are made as separate components, and then assembled. They may all be injection moulded from Plantic (RTM). The sponge 106 is also made separately, as with the embodiments of FIGS. 1 and 4.

FIGS. 6 and 7 show an alternative way of securing the expandable plug 106 in the outlet 103 of the narrow end 105 of the collection system 102. In this embodiment, the plug 106 is held by a first pair of rails 150 and a second pair of rails 151. The rails 150, 151 are moulded as part of the collection system 102 and each comprises a pair of spaced raised ridges formed by the localised thickening of the collection system material. The ridges extend from adjacent the outlet means aperture formed in the narrower end 105 toward the larger end 104. The plug 106 is held between the first pair of rails 150 on one side and the second pair of rails 151 on its other side. The plug 106 is prevented from sliding between the first and second pairs of rails 150, 151 by first and second end rails 152 and 153. The first end rail 152 is positioned adjacent a distal end 154 of the first pair of rails 150. The second end rail 153 is positioned adjacent a distal end 155 of the second pair of rails 151. Thus, as the plug 106 has a cross-section of an isosceles trapezium the rails 150, 151, 152 and 153 securely hold the plug within the outlet means 103 of the tapering collection system 102. The ridges are injection moulded with the collection system 102. However, it will be appreciated that the rails 150, 151, 152 and 153 may be moulded separately from the collection system 102 in either a two-stage moulding process or they may be secured to the collection system 102 by adhesive, for example. The rails 150, 151, 152 and 153 are also able to securely hold the expandable plug 106 in position while it expands in the outlet means 103 thereby ensuring that it restricts the flow through the outlet means an appropriate amount to enable the device to function appropriately.

However made, the device 101 is designed to be stored flat and includes automatic opening means (not shown) that open the funnel 102 from a flat configuration to an open configuration.

The features of the present invention ensure that the device is hygienic and very easy to use. The patient can urinate as normal and the device ensures that the flow is controlled such that a sample is effectively collected without overflowing. Further, the patient is not required to interrupt the flow to ensure an appropriate amount is collected.

What is claimed is:

1. A urine collection device comprising:
    a collection system to collect urine voided by a user, said collection system comprising a funnel;
    first and second outlets adapted to allow urine collected by said collection system to drain from said device;
    a transfer passage adapted to transfer urine collected by said collection system to a receptacle;
    said first outlet including a flow rate variation device so constructed and arranged that an initial drain flow rate through said variation device is greater than a second drain flow rate through said variation device, said first outlet being at a base of said funnel, and said flow rate variation device being accommodated in said base, said flow rate variation device comprising an expandable plug which expands on contact with liquid to provide said second reduced drain flow rate;
    said second outlet comprising an overflow outlet adapted to allow urine collected by said collection system to drain from said urine collection device at a third drain flow rate equal to or higher than said initial drain flow rate through said variation device and
    a transfer device attached to a wall of said funnel at a location above said base, said transfer device including said transfer passage and said overflow outlet, and being adapted for connection to said receptacle.

2. A urine collection device according to claim 1, in which said flow variation device is formed of a sponge material.

3. A urine collection device according to claim 2, in which said sponge material is biodegradable.

4. A urine collection device according to claim 1, in which said transfer device has a connection comprising a connecting collar adapted to receive and retain said receptacle by an interference fit.

5. A urine collection device according to claim 1, in which said transfer device has a connection comprising a screw thread for securing said receptacle.

6. A urine collection device according to claim 1, in which said device is arranged such that said transfer passage allows urine to flow from said collection system into said receptacle when the urine in said collection system reaches a predetermined level, and said overflow outlet allows urine flow to drain once the level in said receptacle reaches a second predetermined level.

7. A urine collection device according to claim 1, in which the a top of said transfer passage forms a further weir over which urine flows to said overflow outlet.

8. A urine collection device according to claim 1, in which said overflow outlet comprises a passage arranged to at least one side of said transfer passage to divert flow away from said receptacle.

9. A urine collection device according to claim 8, in which said overflow passage directs said overflow urine on at least one side of said transfer passage and through an outlet below said receptacle.

10. A urine collection device according to claim 9, in which said outlet below said receptacle is suitably shaped or shielded to direct said overflow away from said receptacle, to avoid the outside of said receptacle coming into contact with urine.

11. A urine collection device according to claim 1, in which said device is so constructed and arranged that, in use, said receptacle is inclined from an upright position.

12. A urine collection device according to claim 1, in which said funnel includes a larger end and a narrower end.

13. A urine collection device according to claim 12, in which said larger end forms a receiving end for positioning adjacent the user in use.

14. A urine collection device according to claim 12, in which said first outlet is at said narrower end.

15. A urine collection device according to claim 1, in which said flow rate variation device is inserted directly into said narrower end of said funnel.

16. A urine collection device according to claim 1, in which said device is readily flushable and biodegradable.

17. A urine collection device according to claim 1, in which portions of said device, except for said expandable plug, are of paper.

18. A urine collection device according to claim 1, in which portions of said device, except for said expandable plug, are of waxed paper.

19. A urine collection device according to claim 1, in which portions of said device, except for said expandable plug, are of a biodegradable polymer.

20. A urine collection device according to claim 1, in which said device is constructed and arranged such that it can be stored flat.

21. A urine collection device according to claim 1, in which said device includes an automatic opening system to open said collection system from the flat storage configuration to an open configuration for use.

22. A urine collection device according to claim 1, in which said flow rate variation device is mounted in said collection system by rails.

23. A urine collection device according to claim 22, in which said rails comprise a first pair of rails adapted to secure one side of said device and a second pair of rails adapted to secure the other side of said device.

24. A urine collection device according to claim 23, in which said rails also comprise a first end rail adjacent said first pair of rails and a second end rail adjacent said second pair of rails.

25. A urine collection device according to claim 1, in which said flow rate variation device is secured in said collection system by adhesive.

26. A urine collection device according to claim 1, in which collection system includes a coupling member to connect said transfer device to said collection system.

27. A urine collection device according to claim 26, in which said coupling member includes a mounting projection that engages with said transfer device.

28. A urine collection device according to claim 27, in which said mounting projection includes a sealing skirt portion that is adapted to form a seal with said transfer device.

29. A urine collection device comprising:
 a collection means to collect urine voided by a user, said collection system comprising a funnel:
 first and second outlet means adapted to allow urine collected by said collection means to drain from said device;
 a transfer passage adapted to transfer urine collected by said collection means to a receptacle;
 said first outlet means including a flow rate variation device so constructed and arranged that an initial drain flow rate through said variation device is greater than a second drain flow rate through said variation device, said first outlet means being at a base of said funnel, and said flow rate variation device being accommodated in said base;
 said second outlet means comprising an overflow outlet means adapted to allow urine collected by said collection means to drain from said urine collection device at a third drain flow rate equal to or higher than said initial drain flow rate through said variation device and
 a transfer device attached to a wall of said funnel at a location above said base, said transfer device including said transfer passage and said overflow outlet means, and being adapted for connection to said receptacle, said transfer passage being generally U-shaped, having a base forming a weir over which urine flows from said collection system into said receptacle.

30. A urine collection device according to claim 29, in which said overflow outlet means comprises a passage arranged to at least one side of said transfer passage to divert flow away from said receptacle.

31. A urine collection device according to claim 30, in which said overflow passage directs said overflow urine on at least one side of said transfer passage and through an outlet below said receptacle.

32. A urine collection device according to claim 31, in which said outlet below said receptacle is suitably shaped or shielded to direct said overflow away from said receptacle, to avoid the outside of said receptacle coming into contact with urine.

33. A urine collection device according to claim 29, in which a top of said transfer passage forms a further weir over which urine flows to said overflow outlet means.

* * * * *